(12) United States Patent  
Kollgaard

(10) Patent No.: US 7,716,989 B2
(45) Date of Patent: May 18, 2010

(54) COLLAPSIBLE GUIDE FOR NON-AUTOMATED AREA INSPECTIONS

(75) Inventor: Jeffrey R. Kollgaard, Kent, WA (US)

(73) Assignee: The Boeing Company, Chicago, IL (US)

( * ) Notice: Subject to any disclaimer, the term of this patent is extended or adjusted under 35 U.S.C. 154(b) by 801 days.

(21) Appl. No.: 11/161,769

(22) Filed: Aug. 16, 2005

(65) Prior Publication Data

US 2007/0057844 A1    Mar. 15, 2007

(51) Int. Cl.
G01N 9/24    (2006.01)

(52) U.S. Cl. .......................................... 73/627
(58) Field of Classification Search .................. 73/627, 73/633, 634
See application file for complete search history.

(56) References Cited

U.S. PATENT DOCUMENTS

| 3,646,683 | A | | 3/1972 | Barzee | 33/434 |
| 4,211,948 | A | * | 7/1980 | Smith et al. | 310/322 |
| 4,304,133 | A | * | 12/1981 | Feamster, III | 73/633 |
| 4,434,659 | A | * | 3/1984 | Kurtz et al. | 73/620 |
| 4,920,658 | A | | 5/1990 | Hile | 33/499 |
| 5,140,784 | A | | 8/1992 | Walsh | 451/495 |
| 5,669,149 | A | | 9/1997 | Meitzler | 33/471 |
| 6,220,099 | B1 | * | 4/2001 | Marti et al. | 73/633 |
| 6,442,856 | B1 | | 9/2002 | Warner | 33/478 |
| 6,614,872 | B2 | * | 9/2003 | Bueno et al. | 378/58 |
| 6,792,809 | B1 | * | 9/2004 | Moore | 73/618 |
| 7,075,084 | B2 | * | 7/2006 | Thompson et al. | 250/341.6 |
| 7,302,851 | B2 | * | 12/2007 | Czerw et al. | 73/620 |
| 2005/0241397 | A1 | * | 11/2005 | Bergman | 73/606 |

FOREIGN PATENT DOCUMENTS

WO    WO 99/26459    5/1999

* cited by examiner

Primary Examiner—Hezron Williams
Assistant Examiner—Tamiko D Bellamy
(74) Attorney, Agent, or Firm—Ostrager Chong Flaherty & Broitman P.C.

(57) ABSTRACT

A system for scanning an aircraft structure includes a collapsible support frame including a mounting member configured to be releasably mountable to the aircraft structure and a moveable member configured to be moveably mounted to the mounting member and to receive a scanning device. The support frame is configured to be positionable in: a collapsed condition in which the mounting member and the moveable member are disposed substantially acutely with each other and an operational condition in which the mounting member and the moveable member are disposed substantially orthogonal with each other.

15 Claims, 4 Drawing Sheets

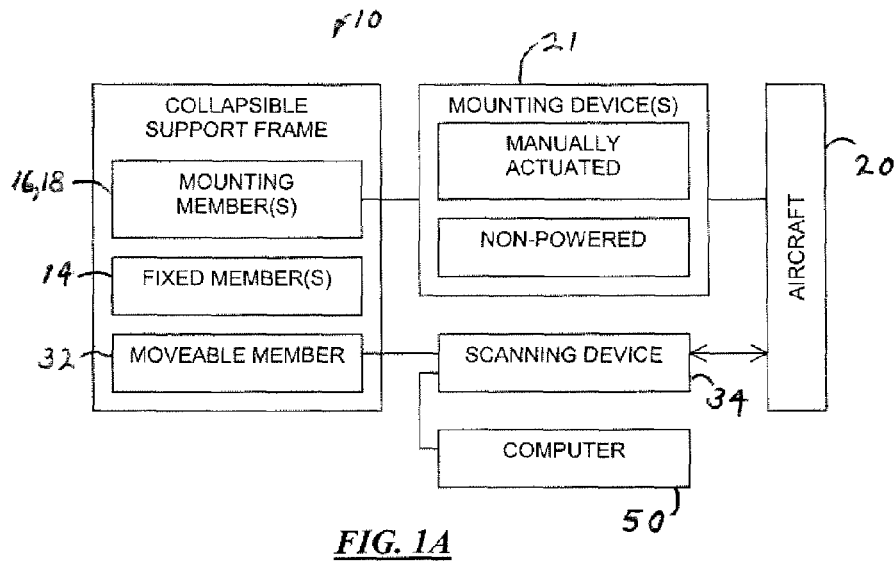
*FIG. 1A*
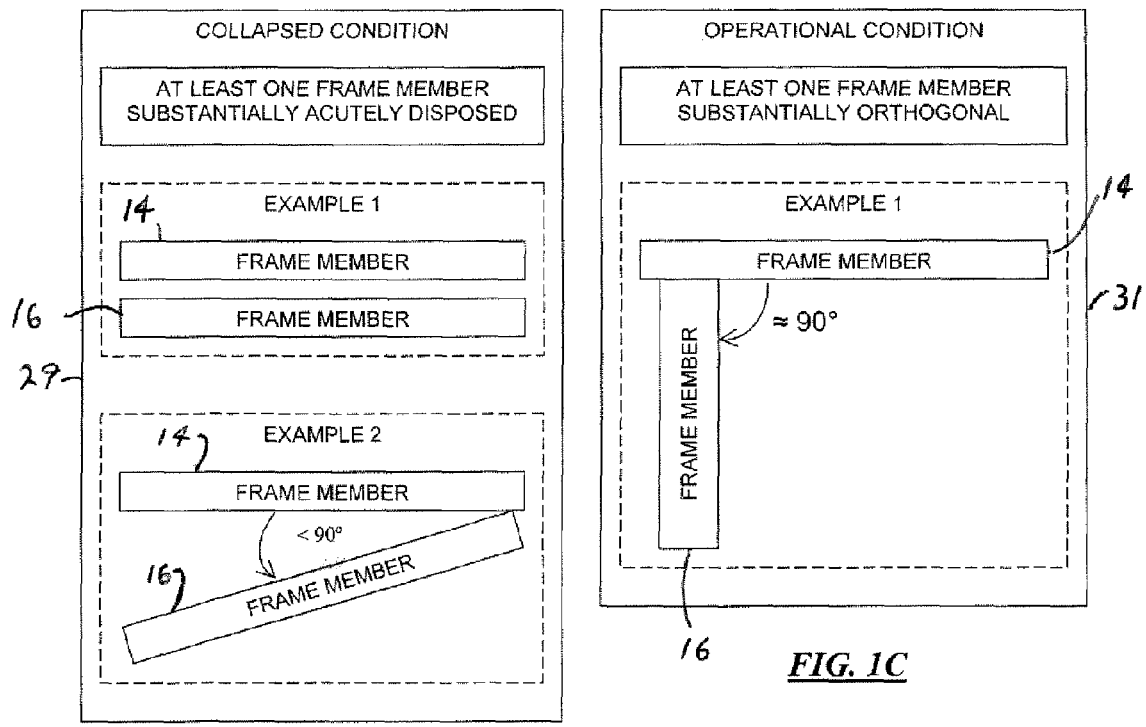
*FIG. 1B*
*FIG. 1C*

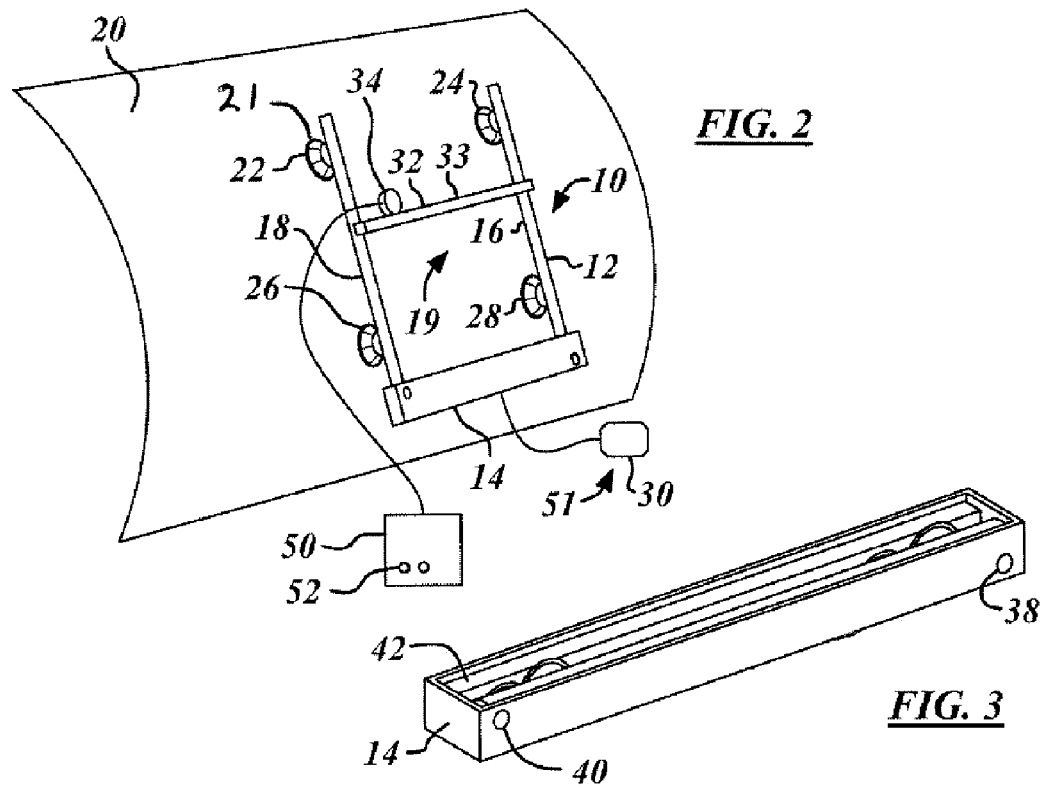
FIG. 2
FIG. 3
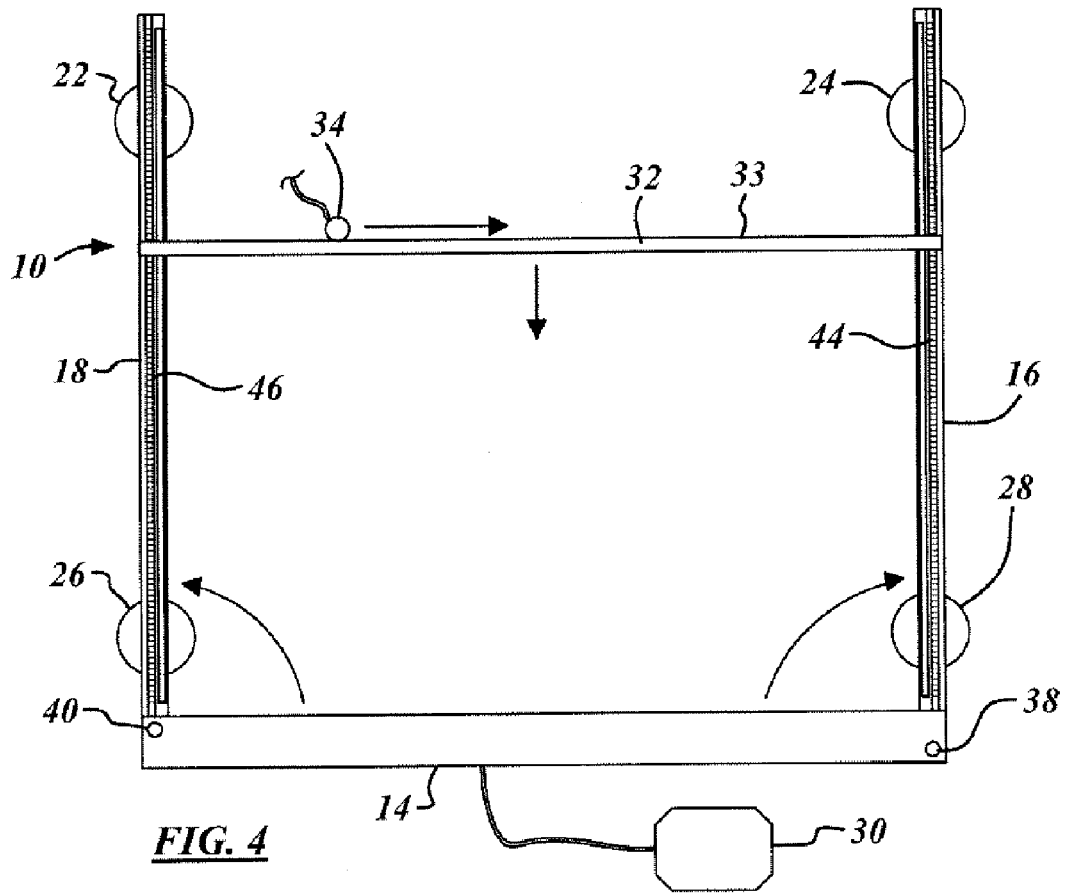
FIG. 4

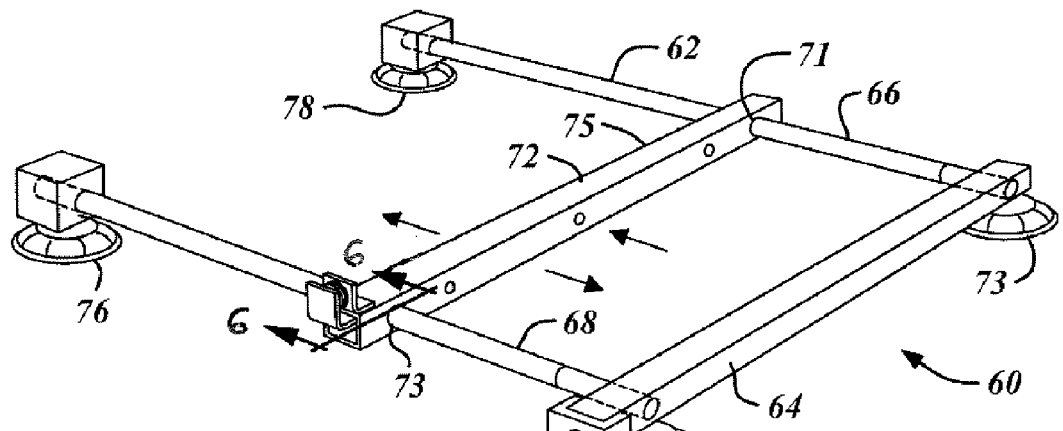
FIG. 5
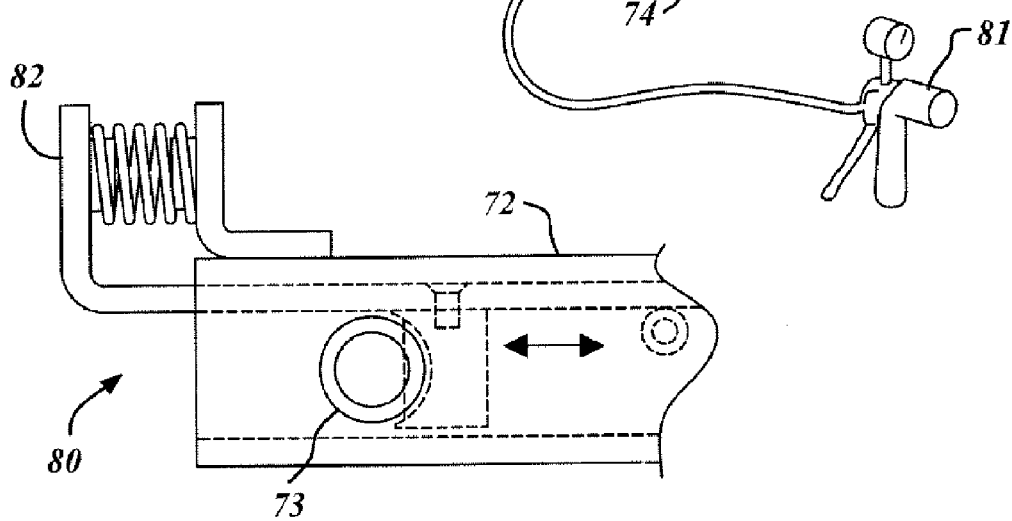
FIG. 6
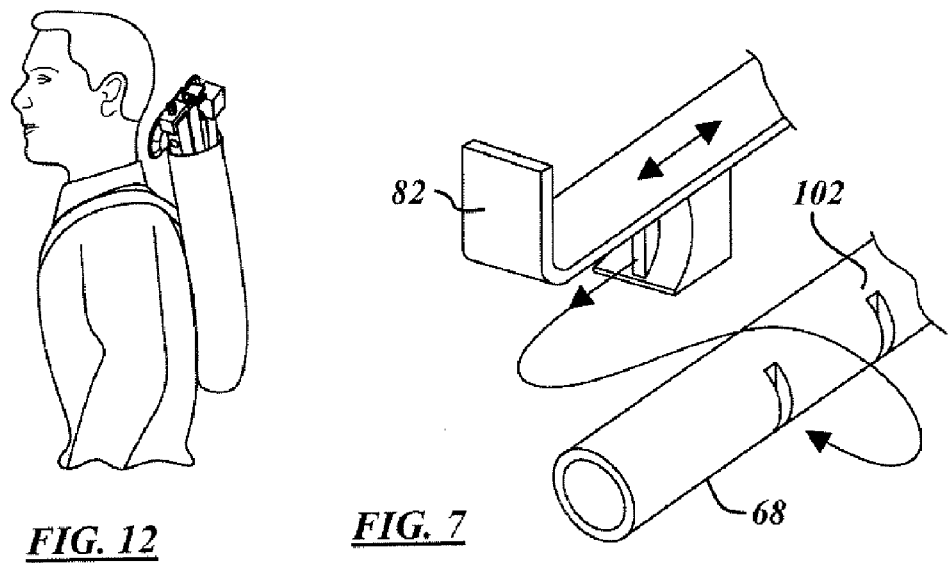
FIG. 12   FIG. 7

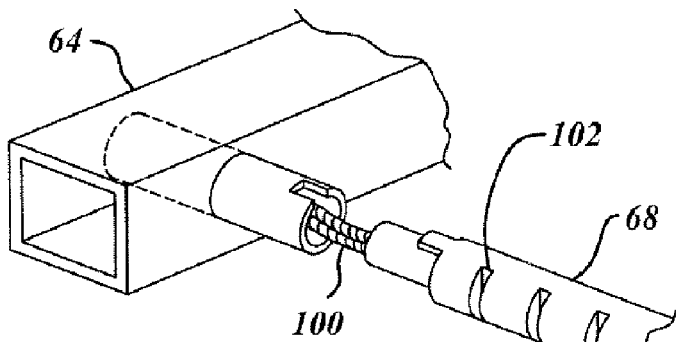
FIG. 8
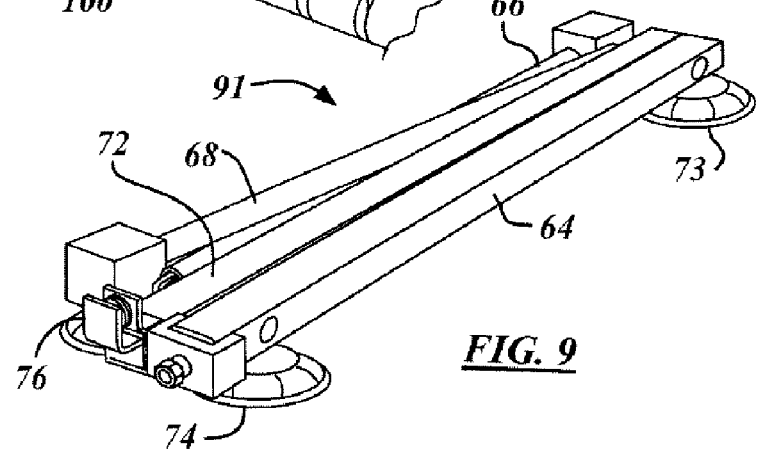
FIG. 9
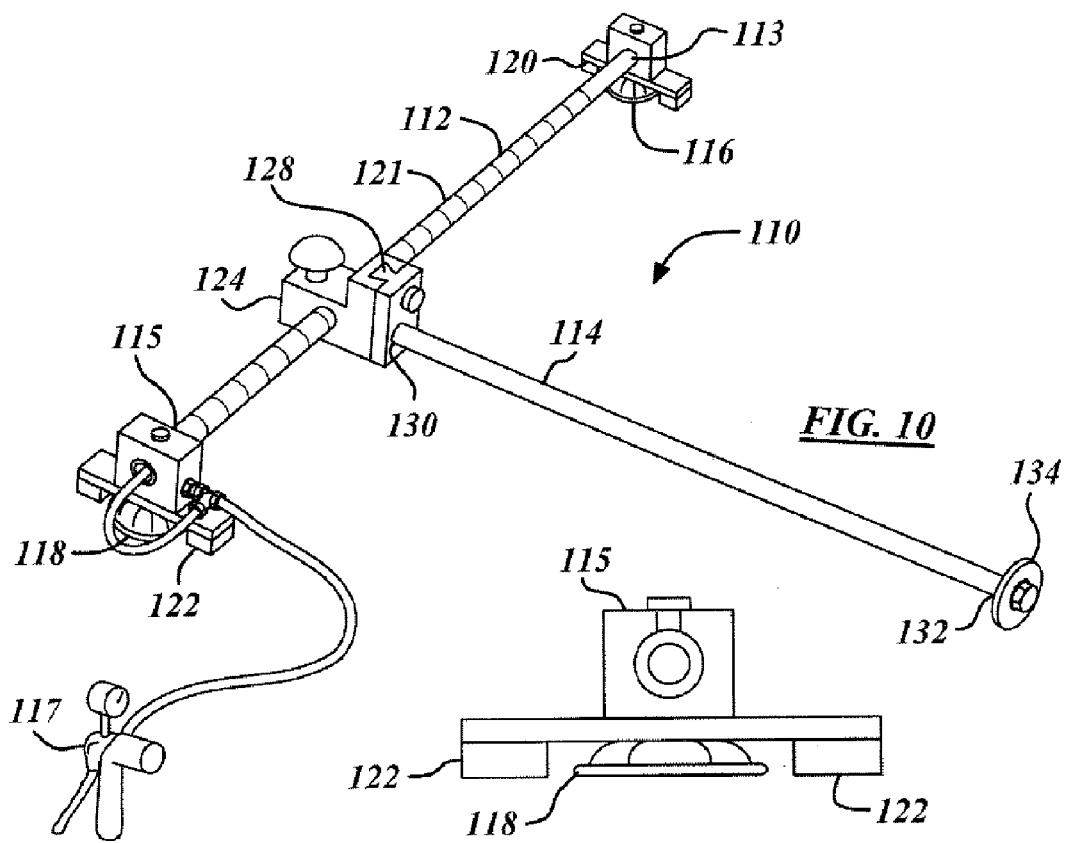
FIG. 10
FIG. 11

COLLAPSIBLE GUIDE FOR NON-AUTOMATED AREA INSPECTIONS

TECHNICAL FIELD

The present invention relates generally to scanning systems and, more particularly, to a collapsible scan guide for non-automated area inspections

BACKGROUND OF THE INVENTION

The inspection of newly-manufactured hardware for aircraft and the like can generally be handled by an inspection facility located close to a manufacturing site having test equipment designed for production compatibility.

In the field, however, in-service inspection is most often performed by portable test equipment for hand scanning. This can be a slow operation when large surfaces are involved. Further, in the case of complex structures, such as bonded aluminum, honeycomb parts with chem-milled skins, stiffeners, access ports and the like, either a hand-scanning technique or some sort of portable small scale scan-record system is required. For large structures with uniform instrument response over large areas, a test technique is required where a wide path can be swept. This currently, however, often requires one or more sensing devices.

Recent studies have found evidence of the limitations of "hand scanning" and the need for some kind of tool to assure a complete coverage of an area. During maintenance of aircraft, there are times when "area" nondestructive inspections are required. There are several situations where this can arise as part of a scheduled maintenance procedure, such as the rudder and elevator ultrasonic inspections specified at certain intervals for different aircraft types.

As a result of damage found on one or more aircraft in a fleet, certain aircraft are selected to undergo surveillance inspections to find damage suspected to exist in locations not exactly known. An example of suspected damage is the disbanding that may arise anywhere in the entire surface of a wing fixed trailing edge panel.

These damage inspections cover entire structure areas having no apparent damage indications, as opposed to the more straightforward practice of scanning localized areas associated with visible impact or lightning strike. It is therefore necessary to "index" the inspection transducer or probe carefully to ensure that the areas are completely covered, leaving no gaps that could contain the small flaws sought. Since the transducer or probe leaves no visible evidence of where it has been, this is no easy task.

The Mobile Automated Scanner (MAUS), or any similar portable C-scan device, is one such tool that assures complete scan coverage. However, airlines have been reluctant to use portable C-scan equipment due to the high cost ($50K to $100K) and the cumbersome nature of the equipment. Repeatedly, airlines have shown their preference for a cheaper, more portable way of accomplishing the same inspection. Smaller carriers, in particular, with only a few airplanes in their fleet, have been reluctant to invest capital in portable C-scans that spend much of their lives collecting dust on a shelf.

An alternative method for assuring complete scan coverage is to use a straightedge to guide the probe across the part. This enables the inspector to scan parallel to underlying stiffeners (a critical technique for interpreting scan signals) and to scan in straight, parallel lines without wandering. It is, however, difficult to hold a straightedge in place while scanning a probe and simultaneously monitoring a screen display. Furthermore, it is difficult to accurately index the straightedge and keep it parallel to the original path after each scan path. And finally, it is nearly impossible to fix the straightedge to the part with double-backed tape or other common adhesive due to the presence of ultrasonic couplant generally found on part surfaces.

There is, therefore, a need for a rapid scanning method for testing aircraft and the like which, at the same time, will accurately and precisely locate any defects or damage in the aircraft structure. Further, there is a need for improved methods and apparatus for scanning aircraft and, in particular, for a guide for a low-cost transportable scanning system that easily attaches to aircraft during a scanning operation.

SUMMARY OF THE INVENTION

In accordance with one embodiment of the present invention, a system for scanning an aircraft structure includes a collapsible support frame including a mounting member configured to be releasably mountable to the aircraft structure and a moveable member configured to be moveably mounted to the mounting member and to receive a scanning device. The support frame is configured to be positionable in: a collapsed condition in which the mounting member and the moveable member are disposed substantially acutely with each other and an operational condition in which the mounting member and the moveable member are disposed substantially orthogonal with each other.

In accordance with another embodiment, a method for scanning an aircraft structure includes placing the support frame in an operational condition in which the members are disposed substantially orthogonal with each other. The mounting member is releasably mounted to the aircraft structure, and a portion of the aircraft structure is scanned with a scanning device coupled to the moveable member. The mounting member is dismounted from the aircraft structure; and the support frame is placed in a collapsed condition in which the members are disposed substantially acutely with each other.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF THE DRAWINGS

For a complete understanding of the invention, there will now be described some embodiments thereof, given by way of example, reference being made to the accompanying drawings, in which.

FIG. 1A is a block diagram of a collapsible guide scanning system coupled to an airplane in accordance with one embodiment of the present invention.

FIG. 1B is a block diagram of a collapsed condition for the collapsible guide scanning system of FIG. 1A.

FIG. 1C is a block diagram of an operational condition for the collapsible guide scanning system of FIG. 1A.

FIG. 2 is a perspective view of a collapsible guide scanning system coupled to an airplane in accordance with one embodiment of the present invention.

FIG. 3 is a frontal view of the collapsible guide scanning system of FIG. 2.

FIG. 4 is a perspective view of the collapsible guide scanning system of FIG. 2 in a collapsed state in accordance with another embodiment of the present invention.

FIG. 5 is a perspective view of a collapsible guide scanning system in accordance with another embodiment of the present invention.

FIG. 6 is a magnified view of a portion of a translating straightedge from FIG. 5 looking in the direction of line 6-6 in accordance with another embodiment of the present invention.

FIG. 7 is a magnified view of a release arm for a translating straightedge in accordance with another embodiment of the present invention.

FIG. 8 is a magnified view of a portion of a fixed horizontal member in accordance with another embodiment of the present invention.

FIG. 9 is a perspective view of the collapsible guide scanning system of FIG. 5 in a collapsed state in accordance with another embodiment of the present invention.

FIG. 10 is a perspective view of a collapsible guide scanning system in accordance with another embodiment of the present invention.

FIG. 11 is a side view of a mounting arm in accordance with FIG. 10.

FIG. 12 is perspective view of the collapsible guide scanning system in a collapsed state and stored in accordance with another embodiment of the present invention.

DETAILED DESCRIPTION

The present invention is illustrated with respect to a collapsible guide scanning system 10 particularly suited to the aerospace field. The present invention is, however, applicable to various other uses that may require welding of various materials together, as will be understood by one skilled in the art. In each of the following figures, the same reference numerals are used to refer to the same components.

Referring to FIGS. 1A and 2, the collapsible guide scanning system 10 includes a collapsible scan support frame 12 or guide with at least one fixed horizontal member 14 and two mounting members or unfolding arms 16, 18 (first mounting arm and second mounting arm respectively). Collectively, the members 14, 16, 18 are frame members. The unfolded frame 12 forms the shape of a U-channel and affixes to an area to be scanned 19 on an aircraft surface 20 through a manually actuated non-powered mounting device 21, e.g. a plurality of suction cups 22, 24, 26, 28 attached through a vacuum provided by a hand squeeze-bulb 30 or pump. Over the two unfolded arms 16, 18 is fitted a moveable member, e.g. translating straightedge 32, so that the apparatus now forms a rectangle with the upper side 33 movable. The translating straightedge 32 provides a guide for a scanning device 34. The scanning device 34 may be moved directly by a user or may be controlled by a controller in a computer or scan control unit 50.

Referring to FIGS. 1B and 1C, block diagrams including a collapsed condition 29 and an operational condition 31 for components of the collapsible guide scanning system 10 are illustrated in accordance with FIG. 1A. For the purposes of this description, a collapsed condition 29 indicates that at least one of the frame members, e.g. one of the unfolding arms 16 and another frame member, e.g. the fixed horizontal member 14, may be "stacked" or "stored" or generally disposed in a substantially acute manner along side each other as represented in Example 1 of FIG. 1B. In addition, the collapsed condition may also indicate that at least one of the frame members 14 may be substantially acutely disposed with respect to another one of the frame members 16, as represented in Example 2 of FIG. 1B. For the purposes of this description, the operational condition 31 indicates a condition in which at least two of the frame members 14, 16 are substantially orthogonally disposed relative to one another.

Referring to FIGS. 2-4, one embodiment of the collapsible guide scanning system 10 is illustrated including the fixed horizontal member 14, two unfolding arms 16, 18 having suction cups 22, 24, 26, 28 coupled thereto, and the translating straightedge 32. The first unfolding arm 16 rotates on the first pivot 38 of the fixed horizontal member 14, and the second unfolding arm 18 rotates on the second pivot 40 of the fixed horizontal member 14.

The fixed horizontal member 14 includes a receiving area 42 for the two arms 16, 18, and may also be sized to receive the removable translating straightedge 32. Thereby, all the components of the system 10 are easily transportable, as illustrated in FIG. 4.

The two unfolding arms 16, 18 rotate at pivots within the fixed horizontal member 14 such that the second arm 18 folds over the first arm 16. The embodied arms 16, 18 each include a straightedge track 44, 46 for controlled movement of the straightedge 32. Further, the arms 16, 18 each include a pair of suction cups 22, 24 and 26, 28 respectively, however, one skilled in the art will realize that numerous numbers of suction cups may be included.

Although illustrated with respect to suction cups, the manually actuated non-powered mounting device 21 may include at least one of a manually actuatable mounting device, a pneumatic mounting device, a non-adhesive mounting device, a non-electric mounting device, or a suction cup.

Once unfolded and fixed to the airplane, a moveable member (fourth member) in the shape of a translating straightedge 32 or other guiding surface, e.g. rounded surface, fits over the two unfolded arms 16, 18 so that the apparatus now forms a rectangle with the upper side movable along tracks 44, 46 on or within the arms 16, 18. Alternately, the straightedge 32 can translate across the scan area using a series of fixed detents keyed to a rack and pinion, a star wheel, an etched distance scale, or some similar arrangement.

The squeeze bulb attachment system 51 holds the frame 12 against the surface of an aircraft through a manually actuated non-powered mounting device 21, e.g. a suction cup. The presence of water or couplant on a part surface may improve suction cup sealing qualities. A few squeezes of the bulb 30 are sufficient to fix firmly the frame to the part, where it remains for an extended time.

The scanning device 34, which may include a transducer, transducer phased array head, eddy current probe, or other sensor and may use ultrasonic, eddy current, or other inspection technology, moves across the straightedge 32. The scanning device may be moved directly by a user or may be controlled by a controller in a scan control unit 50.

The control unit 50 may be coupled to the frame 12 or may be carried separately. The control unit 50 includes indicators 52 for indicating flaws or damage within an airplane component. The indicators, for example, may be lamps. As the scanning unit 34 passes over a surface, the presence of a defect or damage will be indicated by the master indicator. When this occurs, the user can then retrace the path of travel of the scanning unit 34 to locate precisely the location of the defect. Generally, the scanning unit 34 sends and receives signals from the control unit 50.

Referring now to FIGS. 5-9, an alternate embodiment of the collapsible guide scanning system 60 is illustrated including a bungee joint collapsible scan frame 62 having a fixed horizontal member 64 and two collapsible arms 66, 68. The apparatus forms the shape of a U-channel and affixes to an area to be scanned on an aircraft through a number of suction cups 73, 74, 76, 78 and through a vacuum provided by a hand squeeze pump 81 or automatic pump. The two releasable arms 66, 68 (first guide tube and second guide tube) fit into openings 71, 73 in the translating straightedge 72 so that the apparatus now forms a rectangle with the upper side 75 movable. The translating straightedge 72 provides a guide for a scanning device.

Referring to FIG. 6, a close-up view of one embodiment of one side 80 of the translating straightedge 72 is illustrated. The side 80 defines an opening 73 for one of the collapsible arms 68. The collapsible arm 68 is inserted in the opening a particular length, which may be indexed through depression of a release arm 82 coupled to the side 80 and extending therewithin.

The two collapsing arms 66, 68, as illustrated in FIGS. 7 and 8, include bungee attachments (e.g. 100) such that at least one of the arms 68 may be pulled out and folded while still remaining attached to the fixed horizontal member 64 through the bungee attachment 100. For transportation, the arms are bungeed out of the horizontal member 64, the release arm 82 is depressed, and the straightedge 72 is removed, resulting in a transportable collapsed guide 91, as illustrated in FIG. 9.

The embodied arms 66, 68 each include a plurality of spaced index portions 102 or detents such that as the release arm 82 is depressed, the translating straightedge 72 may move along the arm 68, and when the release arm 82 is released, the translating straightedge 72 is held at one of the index portions 102. The release arm 82 thereby may be used to control movement of the straightedge 72. Further, the arms 16, 18 each include a pair of suction cups 73, 74 and 76, 78 respectively, however, one skilled in the art will realize that numerous numbers of suction cups may be included.

Referring to FIGS. 10-11, a collapsible guide scanning system 110 is illustrated in accordance with another embodiment of the present invention. The system 110 includes a single mounting arm 112 and a translating straightedge 114 moving therealong in an orthogonal manner thereto.

As with the unfolding and collapsible arms discussed above, which are also "mounting arms" for the purpose of the present invention, the mounting arm 112 includes a hand-pump 117 and suction cups 116, 118 for attaching the arm 112 to an airplane. The mounting arm 112 includes a first end 113 and a second end 115 whereat the suction cups 116, 118 are positioned. This embodiment also includes pads 120, 122 coupled adjacent to the suction cups 116 and 118 respectively such that, as the suction cups are vacuumed to the airplane, the pads 120, 122 resist over application of vacuum force. The mounting arm 112 also includes gradations 121 such that the translating straightedge 114 may be locked at different heights along the airplane portion to be scanned.

The translating straightedge 114 moveably couples to the mounting arm 112 through a slide mechanism 124 including a release lever 126 for releasing the translating straightedge 114 from a particular gradation 116 along the arm 112. The slide mechanism 124 may also include a detachment joint 128 for detaching the translating straightedge 114 for transportation and storage of the system 110.

A first end 130 of the translating straightedge 114 couples to the slide mechanism 124 or joint 128, and a second end 132 of the translating straightedge 114 includes a roll disc 134 (rolling device) for rolling along the airplane during movement of the translating straightedge 114.

The folded frame is lightweight and can be slipped into a quiver, as illustrated in FIG. 12, that the user wears across his back while climbing ladders or maneuvering around an airplane.

In operation, a method for scanning an aircraft structure includes placing the support frame in an operational condition in which the members are disposed substantially orthogonal with each other. The mounting member is releasably mounted to the aircraft structure; and a portion of the aircraft structure is scanned with a scanning device coupled to the moveable member. The mounting member is dismounted from the aircraft structure; and the support frame is placed in a collapsed condition in which the members are disposed substantially acutely with each other.

From the foregoing, it can be seen that there has been brought to the art a new collapsible guide scanning system. It is to be understood that the preceding description of one embodiment of the present invention is merely illustrative of some of the many specific embodiments that represent applications of the principals of the present invention. Numerous and other arrangements would be evident to those skilled in the art without departing from the scope of the invention as defined by the following claims.

What is claimed is:

1. A system for scanning an aircraft structure, the system comprising a collapsible support frame including:
    a mounting member including a mounting device coupled to said mounting member and configured to be releasably mountable to the aircraft structure and configured to be releasably mountable to the aircraft structure said mounting member comprising at least one of said mounting devices coupled thereto for releasably mounting said mounting member to the aircraft structure; and
    a moveable member coupled to said mounting member and releasably engageable with said mounting member wherein said moveable member is configured to be moveably mounted to said mounting member and to receive a scanning device; and
    a scanning device comprising at least one sensor;
    the support frame configured to be positionable in:
    a collapsed condition in which said mounting member and said moveable member are coupled and disposed substantially acutely with each other; and
    an operational condition in which said mounting member and said moveable member are coupled and disposed substantially orthogonal with each other.

2. The system of claim 1 wherein the support frame includes a pair of mounting members and a fixed member pivotally attached between said mounting members.

3. The system of claim 1 wherein said moveable member is slidably mounted to said mounting member.

4. The system of claim 1 wherein the mounting member comprises at least one manually actuatable non-powered mounting member.

5. The system of claim 1 wherein the support frame comprises a plurality of mounting members, the system further comprising a plurality of mounting devices.

6. The system of claim 1 wherein the moveable member is configured to receive a scanning device so that said scanning device is moveable therealong.

7. The system of claim 6 wherein said moveable member is configured so that said scanning device is moveable in a substantially linear manner.

8. The system of claim 1 further comprising a computer in communication with the scanning device.

9. A collapsible guide scanning system for attaching to and scanning a portion of an airplane comprising:
    a fixed horizontal member;
    a first mounting arm collapsibly coupled to said fixed horizontal member and orthogonal thereto wherein said fixed horizontal member defines a receiving area, such that said first mounting arm collapses into said receiving area and wherein said fixed horizontal member further comprises a receiving guide extending outwardly therefrom for receiving a portion of said first mounting arm wherein said first mounting arm couples to said fixed horizontal member such that said first mounting arm is collapsible relative to said fixed horizontal member while remaining attached and wherein said first mounting arm couples to said fixed horizontal member through a first pivot, such that said first mounting arm pivots for collapsing into said fixed horizontal member;

a second mounting arm collapsibly coupled to said fixed horizontal member and orthogonal thereto such that said second mounting arm is parallel to said first mounting arm;

a plurality of suction cups coupled to a combination of said fixed horizontal member, said first mounting arm and said second mounting arm;

a pump for generating a vacuum between said plurality of suction cups and the portion of the airplane;

a translating straightedge orthogonal to and moveable along said first mounting arm, said translating straightedge moving parallel with respect to said fixed horizontal member wherein said translating straightedge defines a first opening for receiving said first mounting arm and a second opening for receiving said second mounting arm and wherein said translating straightedge comprises a release arm for releasing said translating straightedge from a first height for movement of said translating straightedge to a second height;

a scanning device moveable along said translating straightedge; and a controller receiving signals from said scanning device for inspecting the portion of the airplane.

10. The system of claim 9, wherein said first mounting arm couples to said fixed horizontal member through a bungee attachment.

11. The system of claim 9, wherein said first mounting arm comprises at least one of a height index, a track, a fixed detent keyed to a rack and pinion, a star wheel, and an etched distance scale.

12. The system of claim 9 further comprising a pad coupled to a first end of said first mounting arm for preventing said first mounting arm from contacting an area to be scanned.

13. The system of claim 9 wherein said pump comprises at least one of a hand pump, an electric pump, and a squeeze bulb.

14. A method for scanning an aircraft structure utilizing a collapsible support frame including a mounting member and a moveable member, the method comprising:

placing the support frame in an operational condition in which the members are disposed substantially orthogonal with each other by releasably engaging the moveable member with the mounting member and wherein placing the support frame in the operational condition comprises pivoting the moveable member with respect to the mounting member;

releasably mounting the mounting member to the aircraft structure;

scanning a portion of the aircraft structure with a scanning device coupled to the moveable member;

dismounting the mounting member from the aircraft structure; and placing the support frame in a collapsed condition in which the members are disposed substantially acutely with each other by disengaging the moveable member from the mounting member.

15. The method of claim 14 wherein the sequence of steps is repeatable a plurality of times.

* * * * *